United States Patent
Cole et al.

(10) Patent No.: US 12,191,023 B1
(45) Date of Patent: Jan. 7, 2025

(54) SYSTEMS AND METHODS FOR PATIENT TARGETED THERAPY DEVELOPMENT

(71) Applicant: Flagship Pioneering Innovations VI, LLC, Cambridge, MA (US)

(72) Inventors: Douglas Gowers Cole, Wayland, MA (US); Aaron Garth Day-Williams, Cambridge, MA (US)

(73) Assignee: FLAGSHIP PIONEERING INNOVATIONS VI, LLC, Cambridge, MA (US)

(*) Notice: Subject to any disclaimer, the term of this patent is extended or adjusted under 35 U.S.C. 154(b) by 0 days.

(21) Appl. No.: 18/166,251

(22) Filed: Feb. 8, 2023

Related U.S. Application Data (63) Continuation of application No. 16/370,719, filed on Mar. 29, 2019, now abandoned.

(60) Provisional application No. 62/650,959, filed on Mar. 30, 2018.

(51) Int. Cl.
*G16H 20/40* (2018.01)
*G16H 50/30* (2018.01)

(52) U.S. Cl.
CPC ............ *G16H 20/40* (2018.01); *G16H 50/30* (2018.01)

(58) Field of Classification Search
CPC ......................... G06Q 50/22–24; G16H 20/40
See application file for complete search history.

(56) References Cited

U.S. PATENT DOCUMENTS

| | | | |
|---|---|---|---|
| 8,110,560 B2* | 2/2012 | Singh | A61P 21/00 514/44 R |
| 2003/0134776 A1 | 7/2003 | Hakonarson | |
| 2005/0042688 A1 | 2/2005 | Hashemi | |
| 2009/0169535 A1* | 7/2009 | Marth | A01K 67/0276 424/94.5 |
| 2009/0234262 A1 | 9/2009 | Reid et al. | |
| 2009/0299645 A1 | 12/2009 | Colby et al. | |
| 2012/0231959 A1* | 9/2012 | Elton | G16B 50/00 506/2 |
| 2013/0096212 A1 | 4/2013 | Tammiste et al. | |
| 2015/0329825 A1 | 11/2015 | Herron et al. | |
| 2019/0105311 A1 | 4/2019 | Cacace et al. | |
| 2019/0105498 A1* | 4/2019 | Tang-Schomer | C12M 35/02 |
| 2019/0127736 A1 | 5/2019 | Thibonnier | |
| 2019/0185816 A1 | 6/2019 | Herron et al. | |
| 2019/0321415 A1 | 10/2019 | Fu et al. | |

FOREIGN PATENT DOCUMENTS

| | | | | |
|---|---|---|---|---|
| WO | WO 20030169535 | * | 3/2003 | C12Q 1/68 |

OTHER PUBLICATIONS

"A strategy to discover genes that carry multi-allelic or mono-allelic risk for common disease: a cohort allelic sums test (CAST)"; Morganthaler et al.; Feb. 3, 2007 (Year: 2007).*

Burke, J. F., et al., "Three simple rules to ensure reasonably credible subgroup analyses", Research Methods & Reporting, 2015, 5 pages.

(Continued)

*Primary Examiner* — John A Pauls (57) ABSTRACT

Described herein are platforms for use in targeted therapy development for an individual or group of individuals. Targeted therapy development as described herein comprises developing a therapeutic or therapeutic modality that is specific to or customized to an individual or group of individuals.

20 Claims, 3 Drawing Sheets

(56) References Cited

OTHER PUBLICATIONS

Chiu, Y-D., et al., "Design and estimation in clinical trials with subpopulation selection", Statistics in Medicine, 2018, pp. 4335-4352.

Denne, J. S., et al., "Identifying a Subpopulation for a Tailored Therapy: Bridging Clinical Efficacy From a Laboratory-Developed Assay to a Validated In Vitro Diagnostic Test Kit", Statistics in Biopharmaceutical Research, vol. 6, No. 1, Feb. 2014, pp. 78-88.

"Phenotype definition", Biology On Line (Year: 2021), 2021, 9 Pages.

Fermini, et al., "Clinical Trials in a Dish—A Perspective on the Coming Revolution in Drug Development", SLAS Discovery 2018, Society for Laboratory Automation and Screening, DOI: 10.1177/2472555218775028, pp. 1-12.

Kondej, et al., "Multi-Target Approach for Drug Discovery against Schizophrenia", Int. J. Mol. Sci. 2018, 19, 3105; doi:10.3390/ijms19103105, 30 Pages.

Lam, et al., "Clinical Trial in a Dish—Using Patient-Derived Induced Pluripotent Stem Cells to Identify Risks of Drug-Induced Cardiotoxicity", Thromb Vasc Biol. 2021;41:1019-1031. DOI: 10.1161/ATVBAHA. 120.314695, 13 Pages.

Sayed, et al., "Translation of Human-Induced Pluripotent Stem Cells—From Clinical Trial in a Dish to Precision Medicine", Journal of the American College of Cardiology, vol. 67, No. 18, 2016, ISSN 0735 -1097 / $ 36 .00., 16 Pages.

U.S. Patent and Trademark Office, "Final Office Action Received", U.S. Appl. No. 16/370,719, filed Aug. 11, 2022, 26 Pages.

U.S. Patent and Trademark Office, "Final Office Action received", U.S. Appl. No. 16/370,719, filed Jul. 29, 2021, 11 Pages.

U.S. Patent and Trademark Office, "Non Final Office Action Received", U.S. Appl. No. 16/370,719, filed Dec. 15, 2021, 14 Pages.

U.S. Patent and Trademark Office, "Non Final Office Action Received", U.S. Appl. No. 16/370,719, filed Mar. 1, 2021, 19 Pages.

Warren, et al., "Humanity in a Dish—Population Genetics with iPSCs", Trends in Cell Biology, Jan. 2018, vol. 28, No. 1, https://doi.org/10.1016/j.tcb.2017.09.006, 12 Pages.

Xie, et al., "Deep learning-based transcriptome data classification for drug-target interaction prediction", BMC Genomics 2018, 19(Suppl 7):667 https://doi.org/10.1186/s12864-018-5031-0, 10 Pages.

* cited by examiner

SYSTEMS AND METHODS FOR PATIENT TARGETED THERAPY DEVELOPMENT

CROSS-REFERENCE

This application claims the benefit of U.S. Provisional Application No. 62/650,959, filed Mar. 30, 2018, which application is incorporated herein by reference.

BACKGROUND

Genetic information is being used increasingly in the development of novel therapies for various diseases and abnormalities. Use of genetic information in this type of therapy development shows promise in that, for example, therapies can be potentially tailored to or targeted to an individual or a group of individuals based on their genetic make-up.

SUMMARY

Described herein are systems, methods, and software that make up a platform or that are utilized by a platform for generating groupings of individuals. Platforms described herein in particular are configured to group individuals based on one or both of genetic information and one or more characterization parameters associated with one or more individuals. In some embodiments, a platform develops (or identifies) a targeted therapy at least based in part on one or more groupings that are generated.

In some embodiments, one or more samples are taken from one or more individuals and genetic information and/or one or more characterization parameters are determined from the one or more samples. This information that results from the one or more samples is used, in some embodiments, to generate groupings of said individuals.

In some embodiments, a first grouping of individuals is generated based on genetic information and/or one or more characterization parameters associated with a plurality of individuals. The plurality of individuals, in some embodiments of the platform described herein, are further grouped into a second grouping based genetic information and/or one or more characterization parameters associated with the samples taken from the individuals. That is, in these exemplary embodiments, data from samples is used to group individuals who have already been grouped based on genetic information and/or one or more characterization parameters.

Groupings that are generated by embodiments of the platform described herein are then used, in some embodiments, to develop (or identify) a targeted therapy for the individuals in said groupings. That is, a targeted therapy as described herein is generated (or identified) by a platform described herein utilizing one or more groupings of individuals that are generated based on genetic information and/or one or more characterization parameters associated with the plurality of individuals and/or groupings of individuals based on samples taken from the individuals.

Targeted therapy development as described herein comprises developing a therapy comprising a therapeutic agent and/or a therapeutic modality that is specific to or customized to an individual or group of individuals. In general, a targeted therapy is targeted in that it is specific to an individual. In some embodiments, a targeted therapy is a therapy that exists and is identified (or selected from a plurality of therapies) by the platform as being beneficial and/or optimal for the individual. In some embodiments, a targeted therapy is customized to the individual. A customization may comprise a specific modification of an existing therapy or creation of a new therapy for the individual. Therapy includes therapeutics such as pharmaceuticals and therapeutic modalities such as physical therapy.

In general, a targeted therapy is customized in that it is designed with specificity to an individual or group of individuals. For example, a targeted therapy as described herein, in certain embodiments, addresses one or more qualities, conditions, and abnormalities associated with an individual or group of individuals, wherein the one or more qualities, conditions, and abnormalities may be based on, for example, genetic information and/or characterization parameters that determine the groupings.

For example, a presence of a particular gene in an individual, in some embodiments, is addressed with a targeted therapy generated by the platforms described herein. For example, a presence of a particular gene associated with a grouping of individuals, in some embodiments, is addressed in an individual from said grouping with a targeted therapy generated by the platforms described herein. In some embodiments, the exemplary individual within said grouping may not him or herself possess the gene associated with the grouping.

In some embodiments of the platforms described herein one or more of the following are carried out: (1) Collection of characterization parameter data for a population, (2) Collection of specimens/samples from a population, (3) Extraction of specific characterization parameters relating to individuals from data associated with said individuals, (4) Extraction of genetic information from specimens/samples collected from individuals, (5) Grouping of individuals based on one of: (a) characterization parameter information, (b) genetic information, and (c) characterization parameter information together with genetic information, (6) Extraction of fibroblasts and/or stem cells from a specimen/sample taken from an individual for use in targeted therapy development, and (7) Combining the grouping data with results of fibroblast and/or stem cell based targeted therapy development to develop a targeted therapy or therapies for an individual or a group of individuals within the population from which data is collected.

In general, platforms described herein are configured to extract characterization parameter data, extract genetic data, group individuals, and use the grouping of individuals to guide therapy development so that the therapy developed will be targeted to the individuals or group of individuals.

Described herein is a computer-based system for developing a therapy, said computer-based system comprising: a health record extraction module configured to extract data relating to an individual from a data storage system and determine a characterization parameter of said individual based on said data; a sample processing module configured to determine genetic information associated with said individual based on a sample provided by said individual; a first association module configured to generate a first grouping based on one or more of said characterization parameter and said genetic information; a screening module configured to analyze a therapy induced modulation in a cell culture grown from a cell taken from said sample thereby generating a screening result; and a second association module configured to associate said first grouping with said screening result thereby generating a second grouping, wherein said targeted therapy for said abnormality is developed based on said second grouping. In some embodiments, said data storage system comprises an electronic health record. In some embodiments, said characterization parameter is extracted based on an ICD code. In some embodiments, said characterization parameter is extracted based on a record generated by a health care provider. In some embodiments, said characterization parameter is associated with a biologic sample or cell culture. In some embodiments, said genetic information is determined using a technique selected from a group consisting of PCR, DNA sequencing, epigenetic analysis, and RNA sequencing. In some embodiments, said genetic information is determined using a micro-array. In some embodiments, said sample is selected from a group consisting of a blood sample, a skin sample, a stool sample, a hair sample, and a urine sample. In some embodiments, said cell culture comprises a fibroblast extracted from said sample. In some embodiments, said cell culture comprises a stem cell converted from a fibroblast extracted from said sample. In some embodiments, said targeted therapy is directed to treating epilepsy. In some embodiments, said cell culture comprises a nerve cell and wherein said cell culture is coupled to an electrode configured to generate an electric current that is applied to said nerve cell. In some embodiments, said electric current causes said nerve cell to display one or both of a cell culture characterization parameter and a cell culture genetic information. In some embodiments, said screening result comprises a modulation of one or both of said cell culture characterization parameter and said cell culture genetic information by an agent or intervention.

Described herein is a method for developing a targeted therapy, said method comprising: extracting data relating to an individual from a storage system; determining a characterization parameter of said individual based on said data; determining genetic information of said individual from a sample provided by said individual; generating a first grouping based on one or more of said characterization parameter and said genetic information thereby; analyzing a therapy induced modulation in a cell culture grown from a cell taken from said sample thereby generating a screening result; and associating said first grouping with said screening result thereby generating a second grouping, and wherein said targeted therapy for said abnormality is developed based on said second grouping. In some embodiments, said data comprises an electronic health record. In some embodiments, said characterization parameter is extracted based on an ICD code. In some embodiments, said characterization parameter is extracted based on a note generated by a health care provider. In some embodiments, said characterization parameter is associated with a biologic sample or cell culture. In some embodiments, genetic information is determined using a technique selected from a group consisting of PCR, DNA sequencing, epigenetic analysis, and RNA sequencing. In some embodiments, said genetic information is determined using a micro-array. In some embodiments, said sample is selected from a group consisting of a blood sample, a skin sample, a stool sample, a hair sample, and a urine sample. In some embodiments, said cell culture comprises a fibroblast extracted from said sample. In some embodiments, said cell culture comprises a stem cell converted from a fibroblast extracted from said sample. In some embodiments, said targeted therapy is directed to treating epilepsy. In some embodiments, said cell culture comprises a nerve cell and wherein said cell culture is coupled to an electrode configured to generate an electric current that is applied to said nerve cell. In some embodiments, said electric current causes said nerve cell to display one or both of a cell culture characterization parameter and a cell culture genetic information. In some embodiments, said screening result comprises a modulation of one or both of said cell culture characterization parameter and said cell culture genetic information by an agent or intervention. In some embodiments, said data is extracted from said storage system using a user application on a mobile computing device.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Described herein is a platform designed to group individuals and determine a targeted therapy to provide to individuals based at least in part on their respective grouping. A platform as described herein, in some embodiments, further includes one or more systems, methods, and software. In general, a platform comprises one or more computing devices and/or systems. In general, a computing device comprises a discrete computer such as for example a mobile computing device such as a smartphone. In general, a computing system comprises more components than would be present in a typical standard computing device. For example, a computing system in some embodiments includes separate external user controllers (e.g., a keyboard) and/or external sensors (e.g., wearable sensors) that are communicatively and operably coupled with the computing system processor or processors.

A platform, in some embodiments, comprises at least one server processor (which may be a computing device or computing system) and at least one user processor (which may be a computing device or computing system) that are communicatively linked (and in some embodiments operably linked). It should be understood that a computing system and or device as described herein in certain embodiments of the platform includes software configured to carry out certain functions. Such software may be in the form of, for example, a user application configured to provide an interactive user interface. For example, in some embodiments of the platform, a user has a smartphone including an application that provides an interface for entering data and/or receiving sensed data (such as from a wearable monitoring device). In this example, a platform may include multiple users having multiple user computing devices and/or systems that are integrated into the platform through software. In some embodiments, user software is configured to provide a communication link between users and/or between users and a platform administrator. In some embodiments of the platform a user comprises a healthcare provider and the platform provides a customized health care provider software application that includes a customized health care provider interface.

In some embodiments of a platform as described herein, a platform is configured to extract data from one or more sources, wherein the extracted data is used to group a plurality of individuals.

Extraction of data by a platform as described herein, in some embodiments, includes active extraction of data. In some embodiments, extraction of data performed by a platform comprises passive extraction of data. In some embodiments, extraction of data performed by a platform comprises active extraction of data and passive extraction of data.

An active extraction of data is typically carried out by an extraction software module that is configured to actively extract data from a data source in accordance with a particular algorithm. An active extraction of data typically involves an interaction of an extraction software module with a data source, wherein the extraction software interfaces with the data source so that the extraction algorithm is able to identify specific data and extract that identified data from the data source. For example, an active data extraction software module, in some embodiments, is configured to interface with a database so that the extraction software module accesses the data in the database, and wherein the extraction software module is further configured to extract specific data (which in some embodiments includes all of the data in the data base). For example, in some embodiments, an extraction software module is configured to interface with an electronic health record ("EHR") system which contains multiple EHRs of multiple individuals. In the same example, in some embodiments, an extraction software module is configured to extract data from a specific EHR of a specific individual (or individuals), and, in some embodiments, the active data extraction software module is configured to extract specific data from the specific individuals EHR.

A passive data extraction module is configured to receive a transmission of data from a data source. In some embodiments, a passive data extraction module is configured to interface with a data source such as a data base, and in some embodiments, a passive data extraction module is configured to receive data without interfacing directly with the data source. In embodiments, wherein a passive data extraction module does not interact directly with a data source, it is also known as a data ingestion module.

Once, data is extracted or ingested by an embodiment of a platform described herein, the data is used to group individuals who are associated with the extracted and/or ingested data.

In embodiments of the platform, a grouping of a plurality of individuals is based, at least in part, on genetic information and/or characterization parameters associated with the plurality of individuals that are to be grouped into respective groupings.

In some embodiments, groupings are generated by embodiments of the platform described herein based, at least in part, on samples taken from a plurality of individuals. In some embodiments, a sample comprises cells from the individuals used to generate one or more cell cultures. In some embodiments, one or more cell cultures are used for in vitro analysis and data gathering with respect to the cell cultures. In some of these embodiments, cell cultures provide genetic information and characterization parameters associated with the cell cultures.

In some embodiments, one or more targeted therapies, as described herein, are developed based on one or more groupings of individuals. That is, in some embodiments, genetic information and/or characterization parameters used to group individuals and targeted therapies for one or more of the individuals (or groupings of individuals) are developed based at least in part on the groupings.

In general, genetic information comprises information that is, is associated with, and/or derives from the chromosomes, DNA, RNA, and/or proteins of an individual.

Generally, a characterization parameter is any observable or measurable feature or behavior of an individual. A characterization parameter may be found in a health record of an individual such as an EHR. A characterization parameter may also comprise information directly provided by an individual in, for example, a spoken or written format.

Genetic information and characterization parameters as used herein are described in further detail in the following:

Genetic Information

Genetic information from an individual used to group said individual as described herein, in some embodiments, comprises information relating to one or more genes of the individual including information relating to the gene itself as well as expression of the gene. Genetic information includes chromosomal information as well.

In some embodiments, genetic information is derived from, for example, SNP-array, exome sequencing, deep sequencing, RNA sequencing, epigenetic analysis or other genomic sequencing or characterization technique. In some embodiments, genetic information is analyzed using an algorithm such as a machine learning algorithm configured to identify clusters of similar genetic profiles among individuals based on genetic features. Non-limiting examples of these features include SNP, CNV, epigenetic signatures, and RNA expression of specified tissues as they relate to impacted genes previously shown to be associated with disease phenotypes (risk). In some embodiments genetic information is derived from genotype imputation which typically refers to the statistical inference of unobserved genotypes. It should be understood that any sample/laboratory based and/or statistical or advanced analytical (including machine learning) based technique for deriving genetic information is suitable for use with the embodiments of the platform described herein.

Likewise, in some embodiments of the platform described herein, where a cell culture is grown from a sample taken from an individual, genetic information as used herein also includes genetic information associated with the cell culture grown from the sample taken from the individual. As such, in some embodiments, genetic information comprises genetic information relating to one or more genes associated with a cell culture including information relating to a gene itself as well as expression of the gene (i.e., the gene associated with one or more cells from a cell culture).

Non-limiting examples of types of genetic information suitable for use with the platform described herein (taken from either individuals or cell cultures) includes DNA information (including mitochondrial DNA), RNA information, hybridizing sequence information, and information related to expressed proteins. Genetic information, in some embodiments, comprises named genes or gene clusters such as, for example the BRCA1 gene. In some embodiments, genetic information comprises a disease or predisposition to a disease associated with a presence of a particular gene such as, for example, breast cancer (associated with presence of BRCA1 gene).

In some embodiments, genetic information includes genetic information relating to a group that an individual is associated with. For example, in some embodiments, genetic information comprises familial genetic information comprising, for example, genetic information associated with one or more family members including a parent, a grandparent, an uncle, an aunt, a sibling, and a cousin. In some embodiments, genetic information includes genetic information associated with an ancestry or geographic origin of an individual. In some embodiments, genetic information comprises genetic information associated with a group or a member in a group that an individual is determined to be a member of using the platforms described herein. That is, in some embodiments, once an individual is grouped with other individuals using the platforms described herein, additional genetic information associated with one or more other individuals within the group may be associated with the individual.

In some embodiments, samples from which genetic information is extracted are generally prepared as follows: A sample in the form of, for example, a biologic specimen is taken from an individual that contains DNA. DNA is extracted from the specimen and the DNA containing samples are normalized. DNA is then prepared for exome extraction. A unique identifier is added to each DNA fragment during library preparation to facilitate multiplexed exome extraction and sequencing. Exome fragments are bound to beads and non-specific DNA fragments removed by a series of stringent washes. DNA is PCR amplified and quantified by qRT-PCR. Samples are then sequenced using standard sequencing techniques.

In some embodiments, sequenced DNA taken from samples provided by individuals is further analyzed in order to identify sequence variants useful in targeted therapeutic development. In some embodiments, analysis further includes sequence alignment, variant identification, and genotype assignment of sequenced DNA taken from said samples. In a further analysis step, sequences are annotated and functional variants are identified.

Characterization Parameters

A characterization parameter used by the platforms described herein is generally a physiologic feature of an individual that may be, for example, measured, sensed, and/or observed. Non-limiting examples of a characterization parameter include age, height, weight, gender, ancestry, region of origin, hair color, eye color, blood type, white blood cell count, hematocrit, heart rate, temperature, blood pressure, spO2, cardiac output, stroke volume, presence of a disease state, a mood or mental state of an individual, as well as characteristics of a sample taken from an individual such as color, turbidity, or electrical conductivity of said sample.

Non-limiting sources of characterization parameters include EHR, user applications on a computing device that is part of a platform as described herein (including apps of the user for whom the characterization parameter(s) is/are collected as well as other users who provide characterization parameters for the user whose characterization parameters are being collected), a sensing device such as a wearable sensor, and/or a laboratory such as a blood work laboratory or an electrophysiology laboratory.

Characterization parameters from an individual used to group said individual as described herein comprise generally observable and/or measurable attributes and physical properties of an individual (aside for genetic properties included in the genetic information of the individual).

Similarly, characterization parameters associated with a cell culture generated from a sample taken from an individual generally comprise observable attributes and physical properties of an individual (aside for genetic properties included in the genetic information of the individual).

In general, characterization parameters for both individuals and cell cultures include: (1) physical parameters and (2) behavioral parameters.

Non-limiting examples of physical parameters from an individual suitable for use as characterization parameters in the platforms described herein include an individual's: height, weight, age, ancestry, gender, BMI, blood pressure, heart rate, stroke volume, urine output, medical history information (including as provided to a health care provider and found in a health record), physical exam findings (including as documented by a health care provider and found in a health record) blood levels (including, for example, complete blood count, electrolyte panel, coagulation panel, and drug levels), urine analysis, one or more diagnoses, one or more medications prescribed to an individual, prognosis of a disease or condition, frequency of recurring disease process (e.g., frequency of seizures), radiology results (including images and radiologist interpretations of, for example, ultrasound, CT scan, MRI, nuclear scan, X-Ray, and angiography), stress test results, EEG results (including the EEG itself as well physician interpretation of same), ECG results (including the EEG itself as well as physician interpretation of same), and family history.

Non-limiting examples of behavioral parameters from an individual suitable for use as characterization parameters in the platforms described herein include activity level, compliance with treatments, routine diet behavior (including, for example, food types as well as calorie counts), tobacco use, illicit drug use, alcohol use, stress management, sleep habits, hygiene practices, employment, and any behavioral information recorded in a health record.

Non-limiting examples of physical parameters from a cell culture suitable for use as characterization parameters in the platforms described herein include cell count, cell density, growth rate, metabolic properties, responses to stimuli (including electrical stimuli), responses to therapeutics.

Non-limiting examples of physical parameters from a cell culture suitable for use as characterization parameters in the platforms described herein include growth patterns, resistance patterns, and genetic transfer.

Embodiments of the platforms described herein are configured to access, extract, and/or analyze data from a health record of an individual including both manually recorded health records (e.g., hand-written health records) and EHR. In some embodiments, components of a platform as described herein are configured to access and extract, and/or analyze data associated with an individual. In some embodiments, platforms as described herein are configured to access, extract, and/or analyze electronic health records on a data storage system comprising, for example, a computing device, cloud based storage, or electronic health record system (e.g., Epic or Cerner). Similarly, in some embodiments, platforms described herein are configured to access, extract, and and/or analyze data (including genetic information) from a data storage system configured to store genetic information. In some embodiments, health record information or other data is accessed, extracted, and/or analyzed from a data storage system comprising a personal monitoring device of an individual such as, for example, a wearable monitoring device (e.g., wristlet or smartwatch based app) or a holter monitor. In these embodiments, one or more software applications are configured to interface with computing device, cloud based storage, or system and perform one or more of: (1) access data, (2) extract data, and (3) analyze data.

Targeted Therapy

Embodiments of the platforms described herein are configured to develop or identify a therapy that is targeted to or customized to a particular individual or group of individuals. A therapy, in some embodiments, comprises a therapeutic, in some embodiments, comprises a therapeutic modality, and, in some embodiments, comprises a combination of a therapeutic and a therapeutic modality.

Non-limiting examples of a therapeutic as developed (or identified) by the platforms described herein include pharmaceutical compositions, food and diet based remedies, and nutritional supplements. Pharmaceutical compositions may include, for example, Antipyretics, Analgesics, Antibiotics, Antiseptics, Antipsychotics, Anticonvulsants, Mood stabilizers, Hormone replacements, Contraceptives, Stimulants, Beta-blockers, Chemotherapeutics, Tranquilizers, and Statins (and other cholesterol lowering agents).

Non-limiting examples of a therapeutic modality as developed by the platforms described herein include diagnostic techniques and devices (including, for example, blood work, blood culture, urinalysis, MRI, CT, EEG, ECG, ultrasound, and angiography) as well as movement based therapies, surgeries, mental and/or cognitive therapies, electro-stimulation therapy, radiation therapy, respiratory therapy, exercise/activity based therapy, and phototherapy.

In some embodiments, a targeted therapy is configured to address a disease or other abnormality. Non-limiting examples of diseases include infectious disease, cancer, autoimmune disease, organic brain disease, psychiatric disease, neuromuscular disease, cardiovascular disease, pulmonary disease, renal disease, aging, skin disease, and ocular disease. Examples of diseases for which targeted therapies are generated using the platforms described herein included epilepsy.

Platforms for Grouping Individuals and Developing a Targeted Therapy

Figure 1:
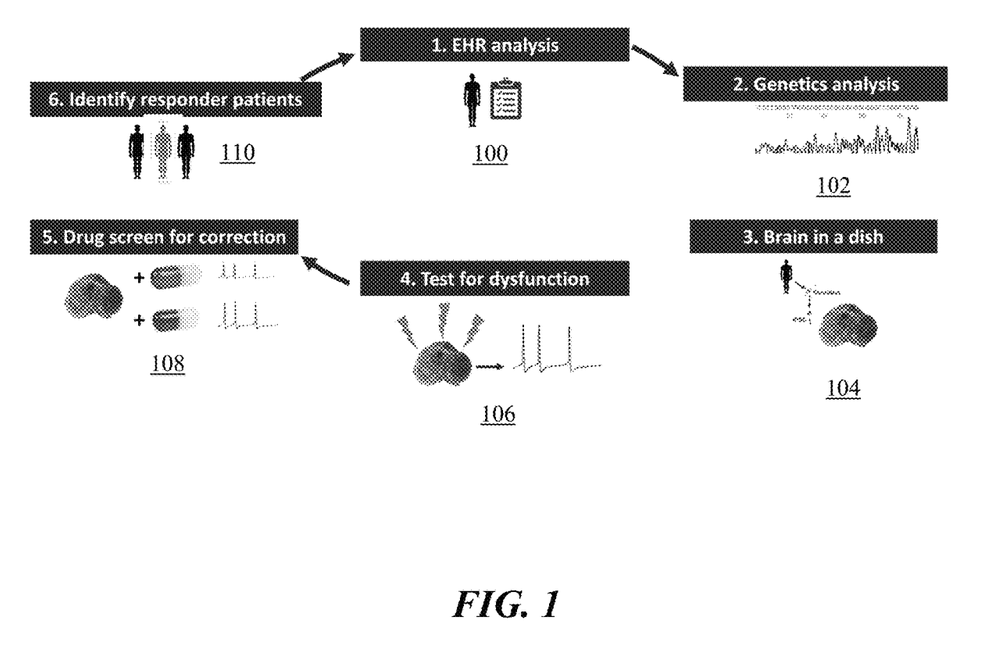
FIG. 1 shows a schematic of an exemplary method for developing a targeted therapy for an individual.

FIG. 1 shows a schematic of an exemplary method for developing a targeted therapy for an individual. In a first step 100, data is extracted from a health record of an individual such as, for example, an EHR. In a step 102, a sample is taken from the individual and an analysis of the genomic material associated with the sample is performed. Non-limiting examples of samples include blood, tissue, sputum, stool, serous fluid, hair, and urine. In some embodiments, a biological sample is created or simulated based on genetic information provided by the patient, such as, for example, using computer simulation or computer modeling. In some embodiments a cell culture is generated from a model cell or derived cell such as, for example, a cell that "mimics" another cell. In a step 104, a cell culture is generated from cells taken from a sample taken from an individual. A cell culture, in some embodiments comprises, for example, fibroblasts and/or stem cells that are extracted from a sample from the individual and grown in an in vitro environment to form a cell culture. In some embodiments, fibroblasts extracted from a sample are converted to stem cells using, for example, an Induced Pluripotent Stem Cell Protocol. In a step 106, the cellular culture is tested for a presence of certain characterization parameters including phenotypes comprising abnormal phenotypes. In some embodiments, a cell culture is further studied to identify one or both of genetic information and characterization parameters in the presence of an external stimulation such as, for example, the application of an electric current. In a step 108, a therapeutic screening of a therapy is carried out on the cellular culture to see if a therapy (from the screened therapies) is identified that affects the one or both of the genetic information and one or more characterization parameters associated with the cell culture. In a step 110, the therapeutic screening data is associated with or correlated with data relating to a population of individuals, such as, for example, genetic information and/or characterization parameters associated with the individuals, in order to identify individuals who have a disease or other condition that responds to or is predicted to respond to a screened therapy found to affect a cell culture.

It should be understood that the steps of the exemplary method shown in FIG. 1, in some embodiments, are carried out in a different order.

In some embodiments, a stem cell is further differentiated in vitro to a nerve cell, multiple nerve cells, or a nerve tissue upon which phenotypic analysis and therapeutic screening analysis is carried out. The methods described herein as applied to a nerve cell, multiple nerve cells, or a nerve tissue is useful in replicating phenotypes of organic brain disease such as epilepsy and for screening therapies to address and prevent symptoms of epilepsy.

A health record as referred to in step 100 of the method of FIG. 1 includes any type of clinical record of patient health. A health record as described herein includes an EHR as well as manually recorded information (e.g., hand written information). Medical information found in a health record includes both structured and unstructured data. Non-limiting examples of structured data found in a health record includes the number of patient visits to a doctor's office, hospital visits, medical diagnoses based on, for example, ICD9/10 codes, laboratory values, procedural codes, diagnostic measures, medications (type, dosing and frequency), and essential vital signs. Non-limiting examples of unstructured data found in a health record includes physician notes including, for example, a summary, an examination, an interpretation of a clinical visit, and other available information includes symptoms, differential diagnoses, a radiological report, and pathological reports. Data is extracted from a health record such as an EHR is done either manually or using a data extracting algorithm.

Extracted data, in some embodiments of the platforms described herein, is analyzed using an algorithm such as a machine learning algorithm configured to cluster similar clinical profiles among individuals based on clinical features (input). Statistically defined patient clusters are defined by, for example, symptomology, comorbidities, drug response, and any of the other readily available features present in a health record.

Genetic analysis of a sample as in step 102 of FIG. 1 generates genetic information as described herein. Genetic information, as described herein, in some embodiments, is derived from a sample taken from an individual (e.g., a blood sample) and, in some embodiments, is derived from a cell culture generated from a sample taken from an individual. In some embodiments, genetic information is derived from, for example, SNP-array, exome sequencing, deep sequencing, RNA sequencing, epigenetic analysis or other genomic sequencing or characterization technique. In some embodiments, genetic information is analyzed using an algorithm such as a machine learning algorithm configured to identify clusters of similar genetic profiles among individuals based on genetic features. Non-limiting examples of these features include SNP, CNV, epigenetic signatures, RNA expression of specified tissues as they relate to impacted genes previously shown to be associated with disease phenotypes (risk). Statistically defined clusters of individuals are defined by, for example, genetic sequence and features including sequence variation and sequence similarity. In some embodiments, clusters of individuals are defined by estimated biological pathway disruption based on genetic analysis (e.g., gene ontology and pathway analysis).

Grouping

In some embodiments, data and information relating to a patient and or groups of patients is used to generate one or more groupings. For example, in some embodiments, health record data extracted from a health record in a step 100 of FIG. 1 and genomic information from a step 102 are combined to form a group which includes phenotype data extracted from the health record and genetic data extracted from samples. In these embodiments, EHR and Genetic information is combined to identify novel patient clusters otherwise indistinguishable by EHR or genetic analysis alone. This group of combined health data and genomic data is further combined, in some embodiments, with in vitro therapy screening data which creates a group that combines cellular information (taken from samples) with patient phenotype and genotype information. In some embodiments, a grouping is established based on a single type of data. For example, in some embodiments, a grouping of individual patients or a grouping of groups of patients is based on phenotypical information. Non-limiting examples of patient phenotype information includes health data from a health record, laboratory data, and radiographic data. For example, in some embodiments, a grouping of individual patients or a grouping of groups of patients is based on patient genotype information derived from a patient sample. Non-limiting examples of means of deriving patient genetic information includes SNP-array, exome sequencing, deep sequencing, RNA sequencing, epigenetic analysis or other genomic sequencing or characterization technique.

Embodiments of the platforms described herein are configured to group individuals based on data relating to the individuals. Data may, for example, comprise one or both of genetic information and one or more characterization parameters relating to the individual. Data may, for example, comprise one or both of genetic information and one or more characterization parameters relating to a cell culture generated from cells taken from a sample taken from an individual. In some embodiments, data used in the process of grouping individuals relates to both individuals as well as cell cultures. For example, a first plurality of individuals may be grouped based on their age (i.e. a characterization parameter) producing an initial grouping. For example, cell culture taken from the first plurality of individuals may be grouped if they show a response to a composition added to their growth medium. For example, in some embodiments, the cell culture data generates data that when associated with the initial grouping of the first plurality of individuals, results in a new grouping of individuals (e.g. if a subset of individuals from the initial grouping had samples that generated cell cultures that generated certain data).

In practice, in some embodiments, a first grouping is generated based on one or both of genetic information and one or more characterization parameters from an individual and a second grouping is generated based on one or both of genetic information and one or more characterization parameters from a cell culture. In some embodiments, the second grouping is associated with the first grouping thereby generating a third grouping (i.e. first, second, and third groupings generated in steps). In some embodiments, a grouping is generated based on one or both of genetic information and one or more characterization parameters from the individual and is further based on one or both of genetic information and one or more characterization parameters from a cell culture (i.e. a single grouping is generated based on data from the individual and data from the cell culture).

Experimental Models

Cell cultures comprising any cell including fibroblasts and/or reprogrammed stem cells are taken from samples in a step 104 of FIG. 1 and their derivatives such as engineered cells or integrated models (spheroids/organoids) are used, in some embodiments, to identify genetic information and/or characterization parameters associated with the cell cultures which in turn are used, in some embodiments, to generate groupings of individuals, and, in some embodiments, to generate targeted therapy for individuals.

In some embodiments, analytical methods are employed that provide biochemical information such as, for example, DNA, RNA, proteomic, metabolomic, or lipidomic data or morphological and phenotypic information such as, for example, electrophysiology, growth, or cellular function data.

Cell cultures are further screened with, for example, pharmacological or molecular compounds that modify biochemical, morphological or phenotypic properties. In these embodiments, an overall output includes novel therapeutic targets for clinically, genetically or experimentally defined patient populations.

Figure 2:
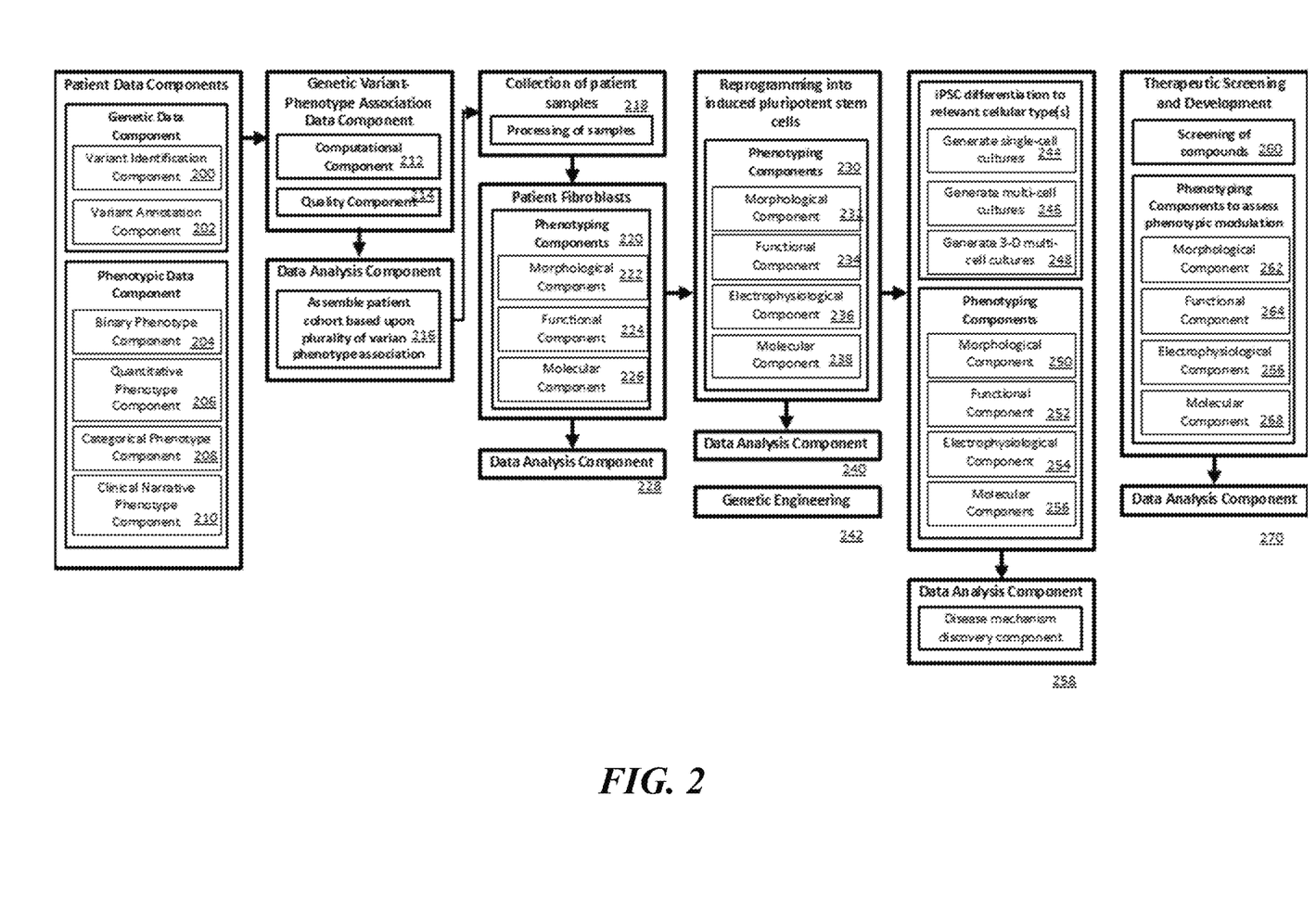
FIG. 2 shows a schematic of an expanded exemplary system directed to a targeted therapy development using one or more components.

FIG. 2 shows a schematic of an expanded exemplary system directed to a targeted therapy development using one or more components. It should be understood that embodiments of platforms described herein comprise one or more components of the exemplary system of FIG. 2. It should be further understood that a system or method as described herein in some embodiments comprises one or more of a computer-based component, a mechanical-based component, a human-based component (including steps and/or processes carried out by a human), and a biochemical-based component.

As shown, the system of FIG. 2 comprises multiple components. A Patient Data Component is configured to extract and process patient health record and genetic data and comprises a Genetic Data Component and a Phenotypic Data Component.

A Genetic Data Component comprises a Variant Identification Component 200 and a Variant Annotation Component 202. Genetic data that is processed in the system of FIG. 2 is separated into identified different variant groups by the Variant Identification Component 200 and the different variant groups are annotated by the Variant Annotation Component 202.

A Phenotype Data Component generally comprises any approach or tool aimed at capturing a set of observable and/or measurable characteristics of an individual, cell, and/or tissue including interactions of the individual, cell, and/or tissue as a consequence of the interaction of its genotype and environment. Generally, a Phenotype Data Component is configured to include characterization parameters of individuals, tissue, and/or cells as described herein. In the system of FIG. 2, the Phenotype Data Component further comprises a Binary Phenotype Component 204, a Quantitative Phenotype Component 206, a Categorical Phenotype Component 208, and a Phenotype Narrative Component 210. The components 204-210 are each configured to extract data from a health record such as an EHR and organize said extracted data so that it identifies one or more characterization parameters of a patient based on his or her health record (or data located on a personal data monitoring device).

The system of FIG. 2 further includes a Genetic Variant-Phenotype Association Data Component comprising a Computational Component 212 and a Quality Component 214. A Data Analysis Component 216 is configured to identify correspondences between genetic variations found in samples taken from individuals and certain phenotypic expression. In some embodiments, A Data Analysis Component 216 comprises a machine learning algorithm configured to analyze data comprising one or both of genetic information and characterization parameters associated with an individual and/or a cell culture.

The system of FIG. 2 includes a component configured to process patient samples 218. In some embodiments, cell cultures are generated from fibroblasts that are extracted from samples taken from individuals and are processed and/or analyzed using a Phenotype Component 220, a Morphologic Component 222, a Functional Component 224, and a Molecular Component 226. The output of components 220-226 is further analyzed by a Data Analysis Component 228.

A Morphologic Component 222 is generally configured to utilize any analytical method that provides information about the morphology of a cell or tissue (e.g., microscopy), which may be combined with image processing tools and visualization tools to extract quantitative data from cell populations.

A Functional Component 224 is generally configured to utilize any analytical method that characterizes a functional or behavioral aspect of an individual or a functional or behavior aspect of a tissue and/or cell, including cellular function which includes but is not limited to cellular growth, motility, cellular death, metabolic processes, cellular interactions, respiratory function, secretory constituent profile, and response to various environmental stimuli.

Fibroblasts are reprogrammed to pluripotent stem cells and further processed and/or analyzed by a Phenotype Component 230, a Morphologic Component 232, a Functional Component 234, an Electrophysiological Component 236, and a Molecular Component 238. The output of components 230-238 is further analyzed by a Data Analysis Component 240. An exemplary method for preparation of fibroblasts includes: Isolation of lymphoblasts from whole blood or isolation of fibroblasts from skin biopsy. Pathogen testing for mycoplasm will be performed if provided sample has not yet been tested. Initial Somatic Cell Bank (fibroblast, CD34+) will be created if required. A working bank of cells will be cryopreserved. Karyotype will be performed to assess genomic stability and integrity. Molecular characterization (RNA sequencing) of isolated lymphoblasts/fibroblasts will be performed.

An Electrophysiological Component 236 is generally configured to utilize any analytical methods able to characterize electrical properties of cells and tissues. For example, by measuring voltage changes or electric current at baseline and in response to externally or internally applied stimuli. Methods will include but not be limited to patch clamp whole-cell measurements, multi-electrode arrays, and optical methods of recording and stimulating electrophysiological activity.

A Molecular Component 238 is generally configured to utilize any analytical method able to characterize biomolecules in a cell or tissue including but not limited to nucleic acids, lipids, carbohydrates, ions, proteins and any other molecule within a cell.

A Data Analysis Component 240 is configured to analyze data generated by other components of the exemplary system of FIG. 2 including data generated from one or more of the Phenotype Component 230, the Morphologic Component 232, the Functional Component 234, the Electrophysiological Component 236, and the Molecular Component 238, which is analyzed to derive conclusions about the biological status of the tested cells and tissue. The biological status of the phenotyped cells and tissue will be compared between sources to identify correlations between disease status and biological status. Conserved differences in biological status in a disease patient group will represent a therapeutic target for therapeutic screening and development.

Stem cells are differentiated in vitro to relevant cell types by a component that includes a Component for Generating Single-Cell Cultures 244, a Component that Generates Multi-Cell Cultures 246, and a Component for Generating 3D Cell Cultures 248. This differentiation related component further includes a Phenotyping Component that includes a Morphological Component 250, a Functional Component 252, an Electrophysiological Component 254, and a Molecular Component 256. The output of components 250-256 is further analyzed by a Data Analysis Component 258 which is configured to determine disease mechanisms based on received in vitro stem cell data. In some embodiments, RNA sequencing data will be analyzed between cohorts to identify differentially expressed genes.

In some embodiments, conversion of lymphoblast/fibroblast cells to induced pluripotent stem cells occurs via episomal reprogramming or sendai virus. Cells will either be transduced with CytoTune® reprogramming particles or transfected with Epi5™ Reprogramming vectors. Approximately 1 week later (CytoTune®) or 2 weeks later (Epi5™), cells will be plated onto a substrate. Cells will be maintained with medium suitable for induced pluripotent stem cells (iPSCs). After ~4 weeks, putative iPSC colonies are expected to have expanded to a size suitable for transfer. Putative iPSC colonies will be chosen based on their observed morphology and the discretion of the observer. Putative iPSC colonies will be picked and transferred to a substrate. Colonies will be grown for ~1-2 additional weeks and transferred to larger culture vessels. A next step comprises selecting one preferred analysis method to be performed on expanded colonies: Immunocytochemistry (ICC) of OCT4/SSEA4 or SOX2/TRA-1-60 2. TaqMan® iPSC Scorecard™. Colonies will be expanded and cryopreserved at $1 \times 10^6$ cells per vial.

In some embodiments, stem cells are differentiated to a nerve cell, multiple-nerve cells, or nerve tissue. In some of these embodiments, the Electrophysiological Component 254 comprises an electrophysiological interface comprised of a multi-probe electrode array. The array is configured to collect electrophysiological signals from either the nerve cell, the multiple-nerve cells, or the nerve tissue. The array in certain embodiments is further coupled with a processor running software configured to decode cellular responses and instruct feedback stimulation to the array. These embodiments are useful in studying the physiology of and screening therapeutics for organic brain or spine abnormalities including, for example, epilepsy. It should be understood that other interface types are considered suitable with the platforms described herein where such interfaces are configured to modulate a phenotype in a cell culture. Such interfaces comprise mechanical and/or chemical modalities.

Additionally, included is a Therapeutic Screening and Development Component which comprises a Compound Screening Component 260. Therapeutic Screening and Development Component further includes a Phenotyping Component comprising a Morphological Component 262, a Functional Component 264, an Electrophysiological Component 266, and a Molecular Component 268. The output of components 260-268 is further analyzed by a Data Analysis Component 270 which is configured to determine disease mechanisms based on the in vitro screening data.

Computer-Based Systems

Some embodiments of the platform described herein comprise systems including computer-based systems. These embodiments which include computer-based systems include a CPU including a processor and memory which may be in the form of a non-transitory computer-readable storage medium. These system embodiments further include software that is typically stored in memory (such as in the form of a non-transitory computer-readable storage medium) where the software is configured to cause the processor to carry out a function. Software embodiments incorporated into the systems described herein contain one or more modules.

Some of the software embodiments described herein are configured to cause a processor to: access data from a data storage system, extract data from a data storage system, and analyze data from a data storage system.

In various embodiments, a system comprises a computing device or component such as a digital processing device. In some of the embodiments described herein, a digital processing device includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, or stylus. In some embodiments, the input device is a touch screen or a multi-touch screen.

The systems and methods described herein typically include one or more non-transitory computer-readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer-readable storage medium is optionally removable from a digital processing device. In some embodiments, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically, the systems and methods described herein include at least one computer program or use of the same. A computer program includes a sequence of instructions, executable in the digital processing device's CPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer-readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object-oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 3:
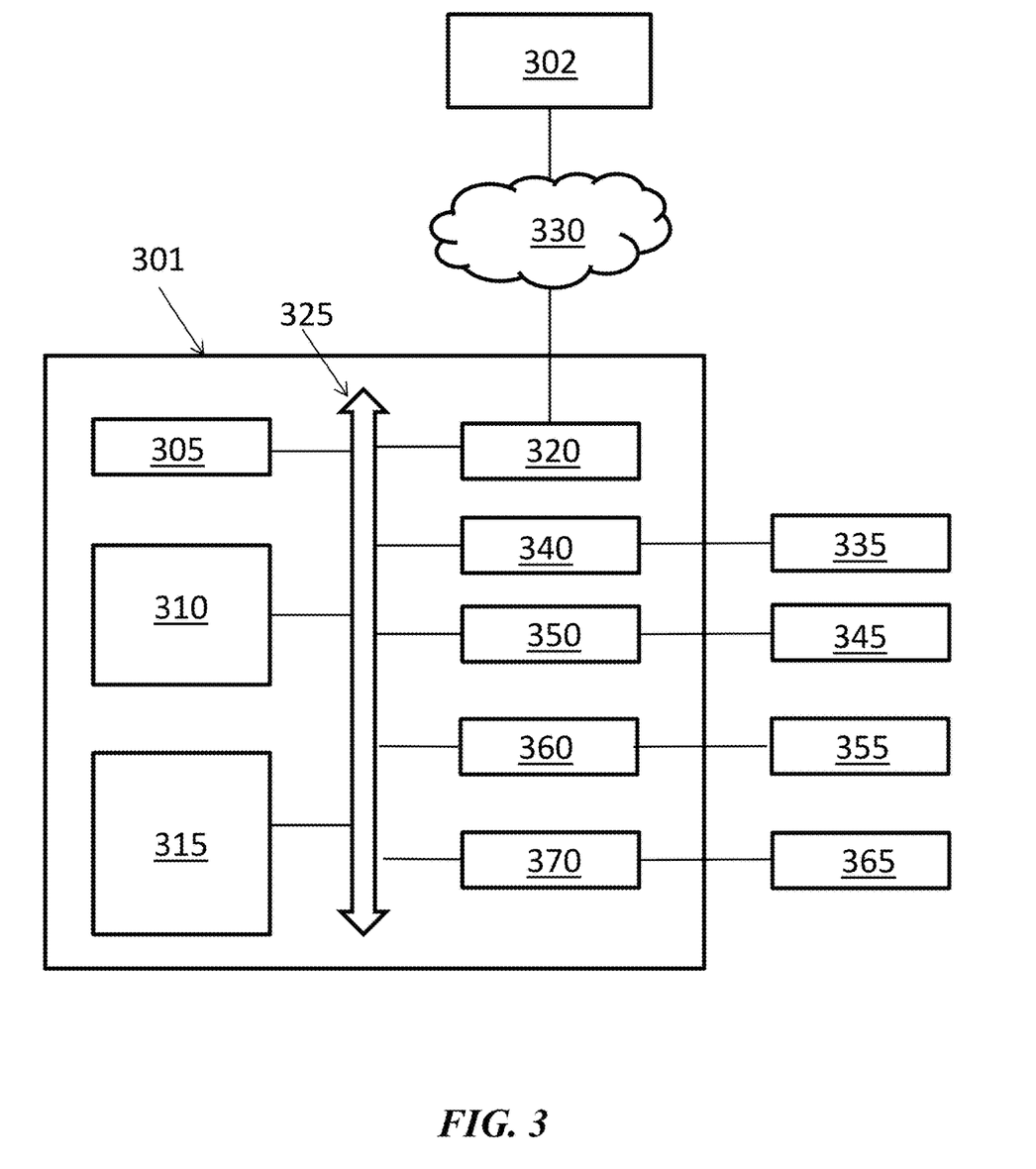
FIG. 3 shows an exemplary embodiment of a system as described herein.

FIG. 3 shows an exemplary embodiment of a computer-based system suitable for use with the platforms described herein. In some embodiments, a system comprises a digital processing device 301. The digital processing device 301 includes a software application configured to process, for example, health record data, sample related data, genomic data, cellular data, and screening data.

The digital processing device 301 may include a central processing unit (CPU, also "processor" and "computer processor" herein) 305, which can be a single core or multi-core processor, or a plurality of processors for parallel processing. The digital processing device 301 also includes either memory or a memory location 310 (e.g., random-access memory, read-only memory, flash memory), electronic storage unit 315 (e.g., hard disk), communication interface 320 (e.g., network adapter, network interface) for communicating with one or more other systems, and peripheral devices, such as cache. The peripheral devices can include storage device(s) or storage medium 365 which communicate with the rest of the device via a storage interface 370. The memory 310, storage unit 315, interface 320 and peripheral devices are configured to communicate with the CPU 305 through a communication bus, such as a motherboard. The digital processing device 301 can be operatively coupled to a computer network ("network") 330 with the aid of the communication interface 320. The network 330 can comprise the Internet. The network 330 can be a telecommunication and/or data network. The digital processing device 301 includes input device(s) 345 to receive information from a user, the input device(s) in communication with other elements of the device via an input interface 350. The digital processing device 301 can include output device(s) 355 that communicates to other elements of the device via an output interface 360.

The CPU 305 is configured to execute machine-readable instructions embodied in a software application or module. The instructions may be stored in a memory location, such as the memory 310. The memory 310 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 110 can also include a basic input/output system (BIOS), including basic routines that help to transfer information between elements within the digital processing device, such as during device start-up, may be stored in the memory 310.

The storage unit 315 can be configured to store files. The storage unit 315 can also be used to store operating system, application programs, and the like. Optionally, storage unit 315 may be removably interfaced with the digital processing device (e.g., via an external port connector (not shown)) and/or via a storage unit interface. Software may reside, completely or partially, within a computer-readable storage medium within or outside of the storage unit 315. In another example, software may reside, completely or partially, within processor(s) 305.

Information and data can be displayed to a user through a display 335. The display is connected to the bus 325 via an interface 340, and transport of data between the display other elements of the device 301 can be controlled via the interface 340.

Methods as described herein can be implemented by way of machine (e.g., computer processor) executable code stored on an electronic storage location of the digital processing device 301, such as, for example, on the memory 310 or electronic storage unit 315. The machine executable or machine-readable code can be provided in the form of a software application or software module. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

Non-Transitory Computer Readable Storage Media

In some embodiments, the platforms described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms described herein include at least one computer program or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process for targeting a therapy to a subgroup of individuals having a health-related condition, abnormality, or disease, the process comprising:
   determining respective characterization parameters for individuals based at least in part on data relating to the individuals as extracted from computer storage, wherein the characterization parameters include a physical parameter and a behavioral parameter;
   determining genetic information for the individuals based on respective biological samples obtained or derived from the individuals;
   generating first data representing a first grouping of the individuals, wherein the individuals in the first grouping have the health-related condition, abnormality, or disease, and wherein the first grouping is based at least in part on the respective characterization parameters and the respective genetic information, such that the first grouping includes individuals who share one or more of the characterization parameters and one or more of the genetic information;
   applying a stimulation based on the therapy to respective cell cultures grown from cells taken from respective biological samples obtained or derived from selected individuals in the first grouping;

measuring any respective modulation in the respective cell cultures caused by the stimulation to a characterization parameter or genetic information from among the one or more of the characterization parameters and the one or more of the genetic information defining the first grouping, thereby generating respective screening results for the biological samples;

generating data representing a second grouping of the individuals, such that the second grouping includes individuals from the first grouping who further share one or more of an additional characterization parameter or genetic information correlated with the respective screening results indicating the individuals in the second grouping are predicted to respond to the therapy; and administering the therapy to an individual who shares the one or more of the characterization parameters and the one or more of the genetic information with the individuals in the first grouping and who further shares the one or more of the additional characterization parameter or genetic information with the individuals in the second grouping.

2. The process of claim 1, wherein the physical parameter comprises a cell culture parameter including one or more of cell count, cell density, growth rate, metabolic properties, response to a stimulus, or response to a therapeutic.

3. The process of claim 2, wherein the physical parameter further comprises one or more of height, weight, age, body mass index, blood pressure, heart rate, stroke volume, urine output, blood levels, urine analysis, radiology results, stress test results, electroencephalograph (EEG) results, or electrocardiogram (ECG) results.

4. The process of claim 3, wherein the behavioral parameter comprises one or more more of activity level, compliance with treatments, diet behavior, tobacco use, illicit drug use, alcohol use, stress management, sleep habits, hygiene practices, or employment.

5. The process of claim 2, wherein the respective biological samples include samples selected from the group consisting of a blood sample, a skin sample, a stool sample, a hair sample, and a urine sample.

6. The process of claim 1, wherein the cell cultures include fibroblasts extracted from the respective biological samples.

7. The process of claim 1, wherein the cell cultures include stem cells derived from fibroblasts extracted from the respective biological samples.

8. The process of claim 1, wherein the cell cultures include cells differentiated in vitro from cells derived from the respective biological samples.

9. The process of claim 1, wherein the cell cultures include nerve cells.

10. The process of claim 9, wherein applying the stimulation to the cell cultures comprises applying an electric current to the nerve cells.

11. The process of claim 10, wherein the electric current causes the nerve cells to display the respective modulation of the characterization parameter or the genetic information.

12. The process of claim 11, wherein the therapy is targeted to treat epilepsy.

13. The process of claim 1, wherein applying the stimulation comprises screening with a compound.

14. The process of claim 1, wherein the characterization parameter modulated by the stimulation includes one or more of cell count, cell density, growth rate, metabolic properties, response to a stimulus, or response to a therapeutic.

15. A process for targeting a therapy to a subgroup of individuals having a health-related condition, abnormality, or disease, the process comprising:

determining respective characterization parameters for individuals based at least in part on data relating to the individuals as extracted from computer storage, wherein the characterization parameters include a physical parameter and a behavioral parameter;

determining genetic information for the individuals based on respective biological samples obtained or derived from the individuals;

generating first data representing a first grouping of the individuals, wherein the individuals in the first grouping have the health-related condition, abnormality, or disease, and wherein the first grouping is based at least in part on the respective characterization parameters and the respective genetic information, such that the first grouping includes individuals who share one or more of the characterization parameters and one or more of the genetic information;

applying a stimulation based on the therapy to respective cell cultures grown from cells taken from respective biological samples obtained or derived from selected individuals in the first grouping;

measuring any respective modulation in the respective cell cultures caused by the stimulation to a characterization parameter or genetic information from among the one or more of the characterization parameters and the one or more of the genetic information defining the first grouping, thereby generating respective screening results for the biological samples;

generating data representing a second grouping of the individuals, such that the second grouping includes individuals from the first grouping who further share one or more of an additional characterization parameter or genetic information correlated with the respective screening results indicating the individuals in the second grouping are predicted to respond to the therapy;

outputting the data representing the second grouping as indicative of the subgroup of the individuals having the health-related condition, abnormality, or disease who are predicted to respond to the therapy; and administering the therapy to an individual who shares the one or more of the characterization parameters and the one or more of the genetic information with the individuals in the first grouping and who further shares the one or more of the additional characterization parameter or genetic information with the individuals in the second grouping.

16. The process of claim 15, wherein the characterization parameter modulated by the stimulation includes one or more of cell count, cell density, growth rate, metabolic properties, response to a stimulus, or response to a therapeutic.

17. The process of claim 15, wherein the cell cultures include fibroblasts extracted from the respective biological samples.

18. The process of claim 15, wherein the cell cultures include stem cells derived from fibroblasts extracted from the respective biological samples.

19. The process of claim 15, wherein the cell cultures include cells differentiated in vitro from cells derived from the respective biological samples.

20. The process of claim 15, wherein the cell cultures include nerve cells.

* * * * *